(12) United States Patent
Faccioli et al.

(10) Patent No.: US 10,639,087 B2
(45) Date of Patent: May 5, 2020

(54) HYDRAULIC EXTRUSION SYSTEM

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (Verona) (IT)

( * ) Notice: Subject to any disclaimer, the term of this patent is extended or adjusted under 35 U.S.C. 154(b) by 147 days.

(21) Appl. No.: 15/746,942

(22) PCT Filed: Jul. 29, 2016

(86) PCT No.: PCT/IB2016/054565
§ 371 (c)(1),
(2) Date: Jan. 23, 2018

(87) PCT Pub. No.: WO2017/021850
PCT Pub. Date: Feb. 9, 2017

(65) Prior Publication Data
US 2018/0214193 A1   Aug. 2, 2018

(30) Foreign Application Priority Data
Aug. 3, 2015 (IT) ................. 10201541542

(51) Int. Cl.
A61B 17/88 (2006.01)
A61F 2/46 (2006.01)
A61M 5/145 (2006.01)

(52) U.S. Cl.
CPC ...... *A61B 17/8822* (2013.01); *A61B 17/8825* (2013.01); *A61F 2/4601* (2013.01); *A61M 5/14526* (2013.01)

(58) Field of Classification Search
CPC .................. A61B 17/8822; A61B 17/8825
See application file for complete search history.

(56) References Cited

U.S. PATENT DOCUMENTS

| | | | | |
|---|---|---|---|---|
| 3,112,743 A * | 12/1963 | Di Cosola | .......... | A61B 17/1622 606/80 |
| 5,431,654 A * | 7/1995 | Nic | ..... | A61B 17/8822 606/92 |
| 2004/0092946 A1* | 5/2004 | Bagga | ..... | A61B 17/16 606/93 |
| 2004/0260303 A1* | 12/2004 | Carrison | ..... | A61B 17/3472 606/92 |
| 2005/0070915 A1* | 3/2005 | Mazzuca | ..... | A61B 17/8822 606/93 |
| 2005/0180806 A1* | 8/2005 | Green | ..... | A61B 17/8822 401/119 |
| 2006/0256646 A1 | 11/2006 | Bidoia | | |
| 2007/0010824 A1* | 1/2007 | Malandain | ..... | A61B 17/8822 606/92 |
| 2012/0191101 A1 | 7/2012 | Roth et al. | | |

OTHER PUBLICATIONS

International Search Report dated Oct. 20, 2016 for PCT/IB2015/054565 (2 pages).

* cited by examiner

*Primary Examiner* — Christian A Sevilla
(74) *Attorney, Agent, or Firm* — Tutunjian & Bitetto, P.C.

(57) ABSTRACT

Hydraulic extrusion system for delivering a fluid including drive means, connection means and a delivery unit including a cartridge, wherein the connection means are adapted for allowing the direct connection between the drive means and the delivery unit.

15 Claims, 9 Drawing Sheets

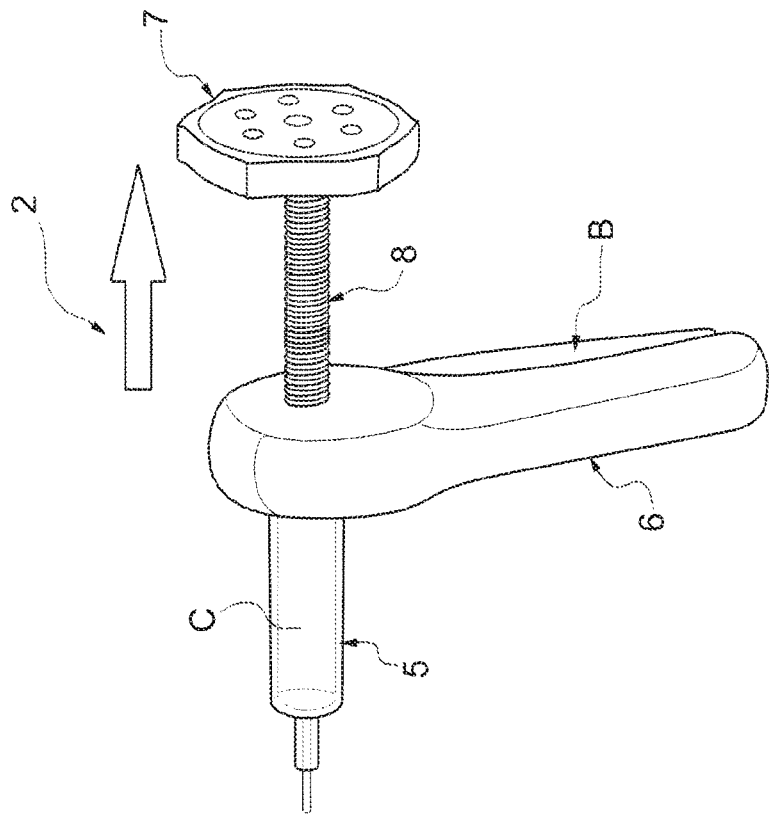
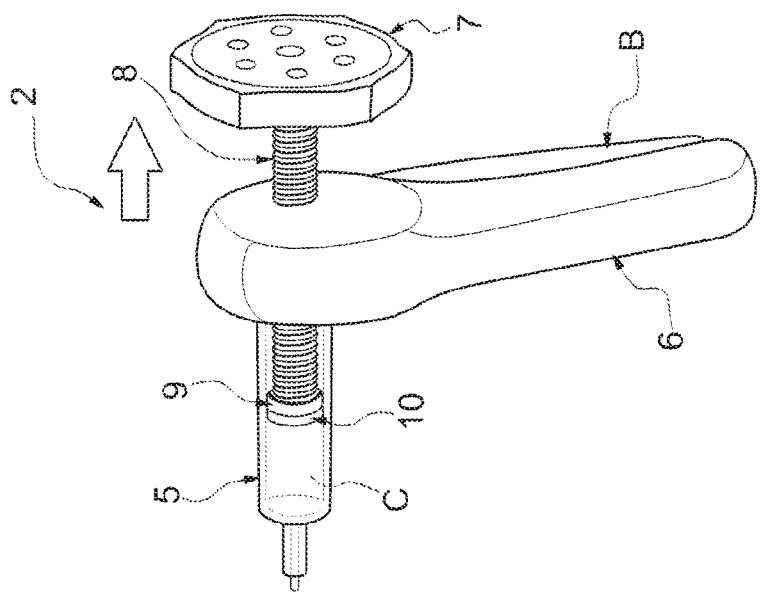

HYDRAULIC EXTRUSION SYSTEM

TECHNICAL FIELD OF THE INVENTION

The present invention concerns a hydraulic extrusion system for delivering a high or low-viscosity fluid.

In particular, the present invention concerns a hydraulic extrusion system for delivering bone cement or other medical fluids inside body locations.

In an alternative version, the present invention concerns a hydraulic extrusion system for inserting a reactant fluid in a hermetic chemical reactor.

The present invention concerns, in yet another alternative version, a hydraulic extrusion system to be used as a remote lubricator.

STATE OF THE ART

In the current state of the art, hydraulic devices for injecting bone cement in a site of a patient are known. Such known devices can foresee the presence of injection means comprising a delivery chamber loaded with bone cement and positioned close to the patient. Such a delivery chamber has an outlet connected to a bone needle and a piston that guides the passage of the cement through the outlet and allows the latter to reach the body location to be treated.

At the opposite end with respect to the delivery outlet, the delivery chamber is connected to a hollow body. Drive means are coupled to such a hollow body through a flexible tube which indeed connects the free end of the hollow body itself to the drive means.

Such drive means guide a fluid through the flexible tube, until the hollow body is reached.

The hollow body has the function of transmitting the pressure generated by the thrust of the fluid to the piston contained in the injection means or in the delivery chamber, thus allowing the bone cement to come out.

In use, the fluid is pushed by the drive means, passes through the flexible tube and enters into the hollow body; at this point the hollow body, through further thrusting means, transmits the pressure generated by the fluid to the piston, which moves, allowing the bone cement contained in the adjacent delivery chamber to come out.

The presence of the hollow body in known hydraulic devices allows the transmission of an increased force, with respect to that initially transmitted to the piston of the delivery chamber: in this way, if the actuation is carried out by an operator, the latter will find it easier to deliver the bone cement.

In addition, the presence of the hollow body contributes to increasing the distance of the operator from the injection site, so that the exposure of the operator to ionizing radiation is reduced.

In the case in which the hollow body is in the form of an inverted syringe, such a body allows manual control over the volume and over the injection speed, as well as immediate interruption of the pressure exerted on the fluid.

Such known devices have proven effective in terms of the multiplication of the delivery and insertion force of bone cement in body locations, but are complex in shape.

The fact that the known device is made up of various parts or portions, moreover, means greater difficulty in assembling it, as well as complexity in the usage and maintenance operations.

In addition, such known devices are extremely bulky, due to the configuration of the elements of which they consist, and consequently they are difficult to handle and to position close to the patient.

Moreover, since such known devices are complex and formed from various components, this increases the weight of the device when inserted in the body of the patient, causing discomfort or pain to said patient.

Some known devices are disclosed by US2012/191101, US2005/070915, US2004/260303.

Therefore, there is a need to obtain hydraulic devices that are simpler, lighter and less bulky, so as to facilitate the delivery operation of the fluid or of the bone cement.

SUMMARY OF THE INVENTION

The technical task of the present invention is to improve the state of the art.

In such a technical task, a purpose of the present invention is to provide a hydraulic extrusion system that is easy to use, within the scope of a constructively simple solution.

Another purpose of the present invention is to provide a hydraulic extrusion system that acts as a force multiplier, thus requiring that the operator exerts a reduced actuation force to overcome the resistance of the fluid to the delivering.

Moreover, another purpose of the present invention is to ensure a minimal vertical bulk. Indeed, the reduced bulk, in case of use in the field of medicine, reduces the risk that the lateral forces, transferred during the extrusion of the cement to the delivery needle, damage the bone in which such a needle is inserted, or the risk of touching the various diagnostic systems arranged close to the treated bone, compromising the sterility thereof.

A further purpose is to provide a hydraulic extrusion system that withstands great pressures and that can be used with most fluids used in the medicine and chemistry field.

In accordance with an aspect of the present invention, a hydraulic extrusion system is provided according to the present application.

The present application refers to preferred and advantageous embodiments of the invention.

BRIEF DESCRIPTION OF THE DRAWINGS

Further characteristics and advantages of the present invention will become clearer from the detailed description of a preferred, but not exclusive embodiment of a hydraulic extrusion system, illustrated for indicating but not limiting purposes in the attached tables of drawings in which:

FIGS. 5a and 5b show two actuation steps of drive means of the hydraulic extrusion system according to the present invention during the insertion operation of the first fluid or hydraulic fluid in them;

DETAILED DESCRIPTION OF THE INVENTION

Figure 1:
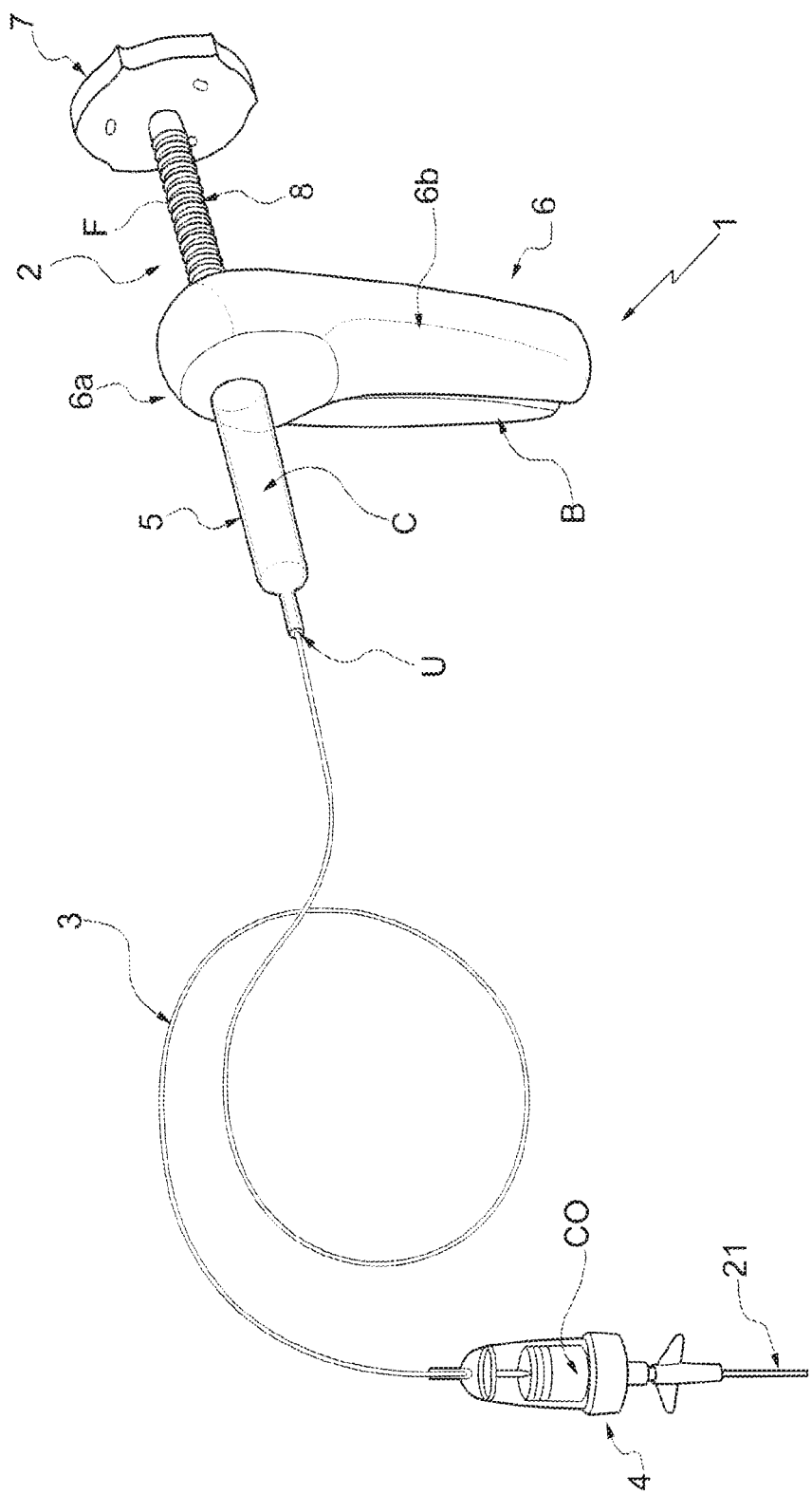
FIG. 1 is a perspective view of a hydraulic extrusion system according to the present invention.

With reference to the attached figures, a hydraulic extrusion system for delivering a viscous fluid is wholly indicated with reference numeral 1.

In the following description, reference will be made to a hydraulic extrusion system for medical-type use, like for example a system adapted for delivering bone cement or a medicated fluid or a contrast liquid or fluid drugs. In particular, such delivery takes place by controlling the delivery thrust very precisely.

However, the scope of protection of the present invention also encompasses further versions of the delivery system in question, for example used in different fields than medicine, without any limitation.

In particular, in a version of the invention, reference is made to a hydraulic extrusion system for inserting a reactant fluid in a hermetic chemical reactor.

The present invention concerns, in another alternative version, a hydraulic extrusion system to be used as a remote lubricator.

The hydraulic extrusion system 1 comprises drive means 2, connection means 3 and a delivery unit 4.

The drive means 2 allow the actuation of the extrusion that takes place through the hydraulic extrusion system 1. In particular, in a version of the invention, bone cement CO is delivered with the hydraulic extrusion system 1.

The drive means 2 comprise a hydraulic pump, for example a water pump or a pump for another hydraulic liquid.

Such a hydraulic pump comprises a syringe 5, a handle 6, a knob 7 and a plunger 8.

The syringe 5 delimits a cavity C inside which a first fluid PF is inserted.

The cavity C constitutes a chamber or space for housing the first fluid PF.

The first fluid PF is an actuator fluid.

Figure 2:
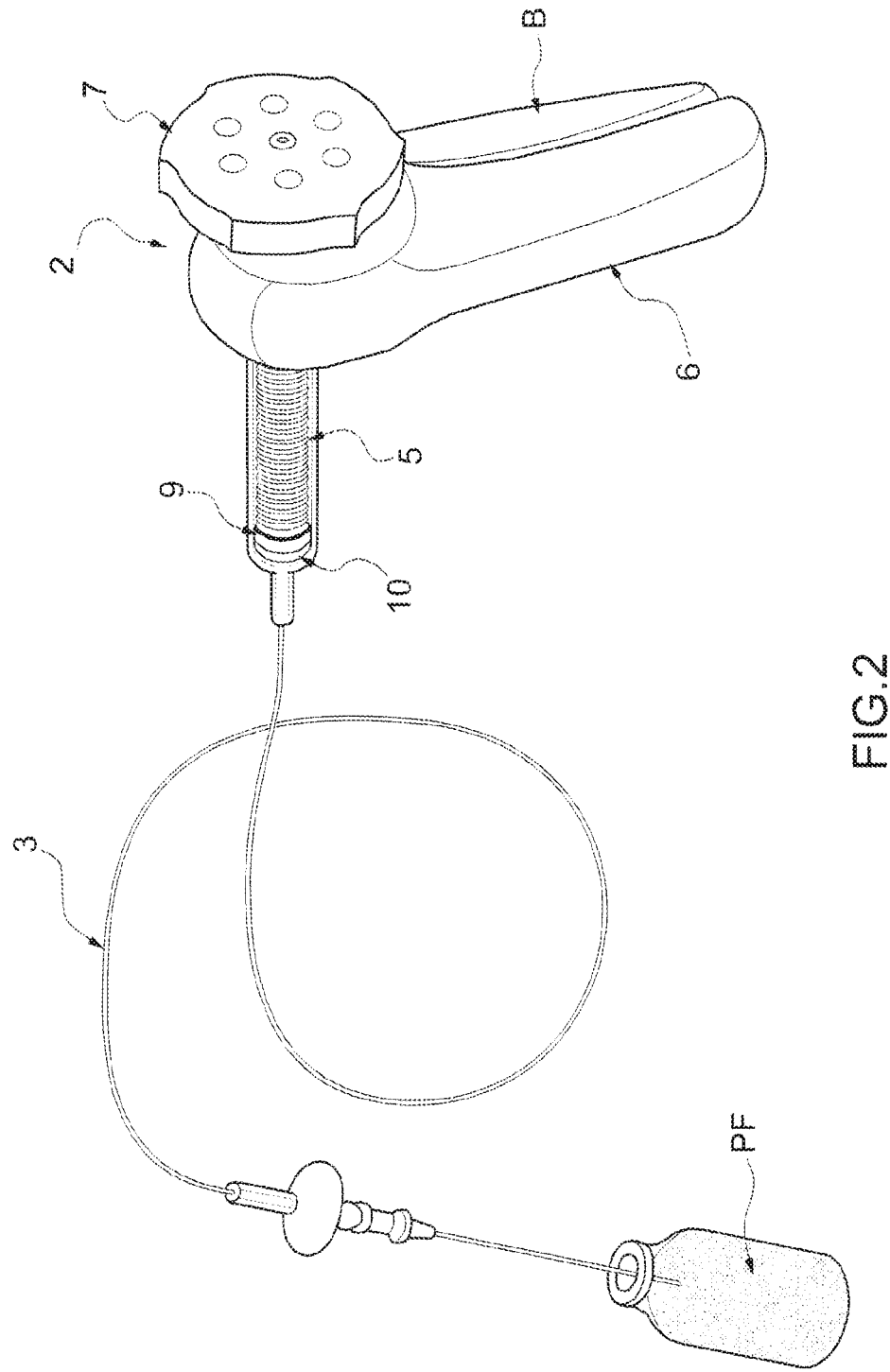
FIG. 2 shows an insertion step of a first fluid or hydraulic fluid inside the drive means.

The insertion operation of such a first fluid PF in the cavity C, as shown in FIG. 2, will be described more clearly hereinafter.

For example, the first fluid PF can be water or saline solution or a hydraulic fluid.

The syringe 5 or the cavity C has, at a first end, a delivery nozzle U and, at a second end opposite the first end, means for fixing to the handle 6.

Through the nozzle U, the first fluid PF can enter or exit into/from the cavity C.

The handle 6, mounted on the syringe 5, allows a good grip of the drive means 2 of the hydraulic extrusion system 1 by the user.

The handle 6 has a substantially elongated configuration equipped with a first portion 6a, adapted for engaging with the syringe 5, and a second portion or handle portion 6b, having a substantially elongated shape, adapted for being gripped by the operator.

At its handle portion 6b, the handle 6 comprises a lever B.

The lever B is an unlocking lever that allows the plunger 8 to be operated according to two ways, as will be described more clearly hereinafter.

The syringe 5 can be connected, in use, to the plunger 8. In particular, the plunger 8 is housed and able to slide inside the cavity C of the syringe 5.

The plunger 8 comprises a first piston 10 and a threaded cylindrical bar. At a proximal end of such a threaded bar, at the first piston 10, a gasket 9 is mounted for the hydraulic seal; at the distal end of the plunger 8, opposite to the proximal end, a knob 7 is mounted.

In a preferred configuration, the knob 7 is in the form of a disc, but other shapes are possible that promote the gripping and actuation thereof by a user.

The first piston 10 is slidably engaged inside the cavity C.

The first piston 10 is hermetically sealed, possibly thanks to the presence of the gasket 9.

Figure 11:
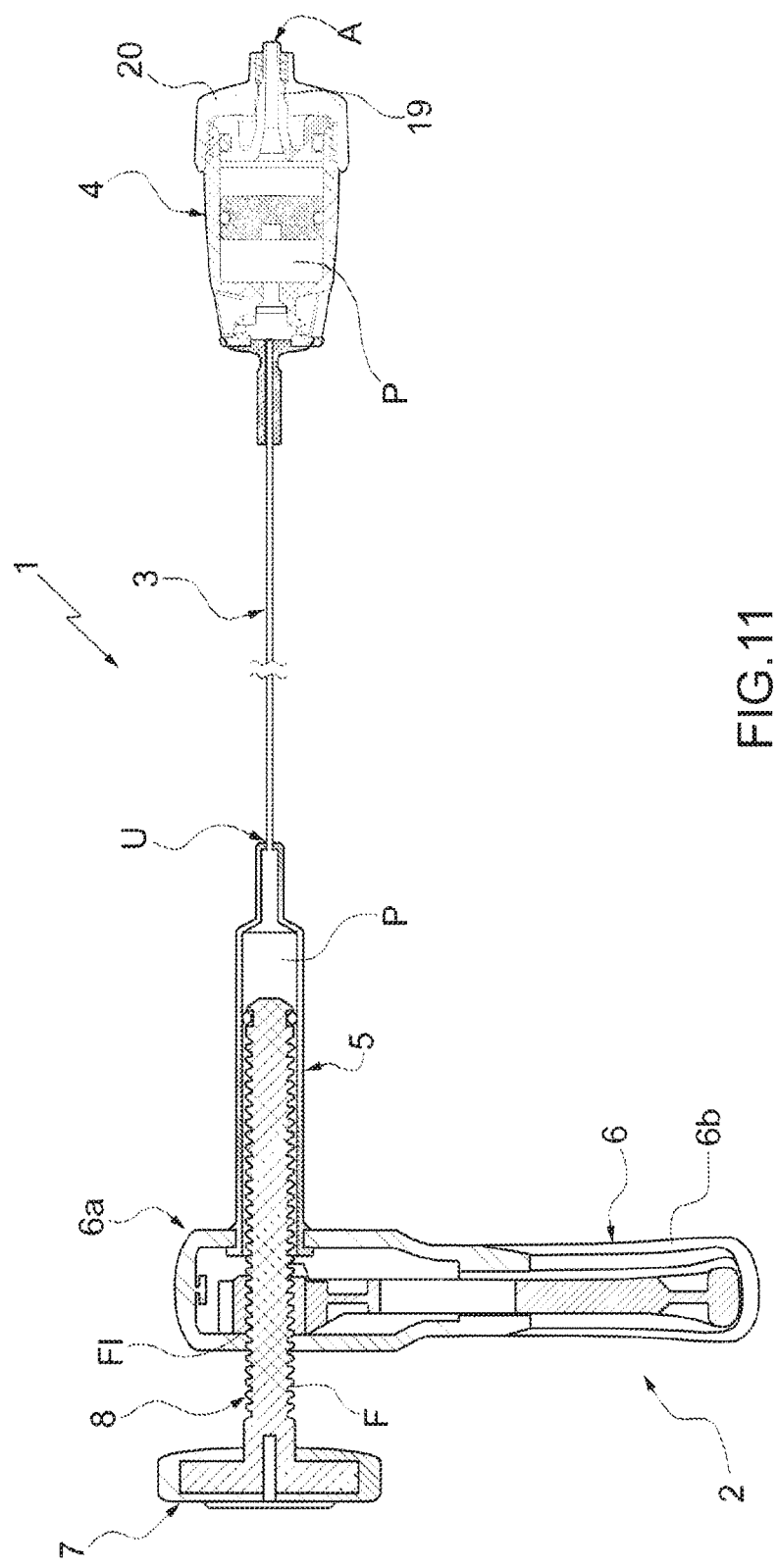
FIG. 11 is a section view of the hydraulic extrusion system according to the previous figures.

The plunger 8 or the threaded cylindrical bar thereof can comprise a threading F, which engages in an internal threading FI, as shown in FIG. 11, present in the handle 6 or rather in the first portion 6a thereof.

In one way of operating, the first piston 10 can be actuated in translation by the plunger 8. As illustrated in FIGS. 2, 5a and 5b, such a way of operating is foreseen for the insertion of the first fluid PF in the cavity C of the syringe 5. During such an operation, the lever B is pressed by the user and is in an unlocked configuration.

Following the compression of the lever B by the user, indeed, the threading F is disengaged or disconnected from the internal threading FI of the handle 6, creating a clearance between such threadings F, FI that allows a substantially linear translation of the plunger 8. Such a substantially linear translation of the plunger 8 takes place following a substantially linear traction applied manually to the knob 7.

The traction of the knob 7, and the consequent translation of the plunger 8, creates a depression inside the syringe 5 that allows a first fluid PF, contained for example in a vial, to be drawn back and therefore allows the cavity C to be filled.

Once the syringe 5 is filled with the first fluid PF, it is possible to actuate the plunger 8 and the first piston 10 according to a second way of operating.

During such a second way of operating, the first piston 10 moves inside the cavity generating a force against the first fluid PF and that results in the delivery of the first fluid PF itself.

During this thrusting operation, as stated, the plunger 8 slides inside the cavity C.

In this step, the operator releases the lever B, which is thus in an engaged configuration.

Such an engaged configuration determines the engagement of the threading F of the threaded cylindrical bar of the plunger 8 with the internal threading FI present in the handle 6. The engagement configuration of the threading F in the threading FI is illustrated in FIG. 11.

The engagement of the threading F and of the internal threading FI allows the advancing by rotation of the plunger 8, following a rotation applied manually on the knob 7.

Figure 7:
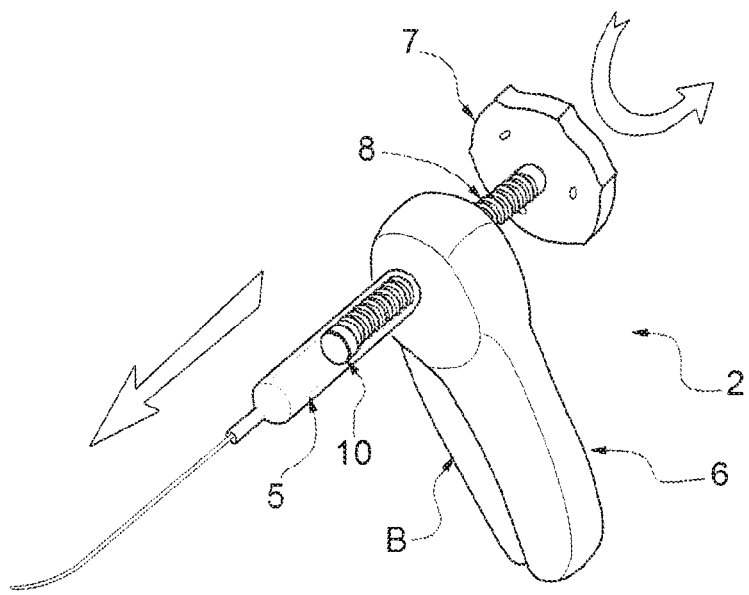
FIG. 7 shows an actuation step of the drive means of the hydraulic extrusion system according to the present invention.

The rotation operation of the knob 7, as shown in FIG. 7, thus leads to the translation of the plunger 8 that pushes the first piston 10 present inside the cavity C, said first piston 10 in turn pressurizing the first fluid PF contained in the syringe 5, leading to it coming out through the nozzle U.

In greater detail, the translation of the plunger 8 takes place thanks to the relative rotation of the threading F inside the internal threading FI of the handle 6.

As a matter of fact, therefore, the translation of the first piston 10, along the cavity C of the syringe 5, pushing against the fluid contained there, is controlled by the knob 7.

During the rotation operation of the knob 7, i.e. during the thrusting operation of the first piston 10, the thrusting operation of the first piston 10 is thus possible through rotation of the knob 7.

The lever B thus comprises a locking or unlocking means for the plunger 8, wherein in the locked configuration the knob 7 is set in rotation to promote the delivery of the first fluid PF by the drive means 2 to the connection means 3, and in the unlocked configuration the knob 7 is set in traction, towards the outside or distally with respect to the syringe 5, to promote the insertion operation of the first fluid PF in the drive means 2.

In greater detail, in the case of locking of the lever B, the plunger 8 can translate following the rotation of the knob 7 and push the first piston 10, so as to promote the delivery of the first fluid PF.

In the case of unlocking of the lever B, the plunger 8 can translate following the pulling of the knob 7, said pulling occurring in the distal direction with respect to the syringe 5 or outwards, so as to promote the drawing of the first fluid PF, and therefore the filling of the syringe 5.

The knob 7 comprises a dynamometric mechanism that allows it to limit the pressure and speed with which the first fluid PF is delivered to a predetermined maximum value. In this way, pressures and speeds that are too high, which can lead to dangerous situations for the patient, like for example the bursting of the delivery unit 4, are avoided.

The maximum tolerated values for pressure and speed are linked to the strength of the hydraulic extrusion system 1 itself.

The knob 7 thus has the purpose of avoiding reaching pressure that can cause structural yielding in the hydraulic extrusion system 1.

When the pressure values exceed a certain maximum threshold, the knob 7 no longer allows the normal rotation operation, but it starts to rotate idly.

The connection means 3 have a first distal end connected to the nozzle U of the drive means 2 and a second proximal end, opposite to the first distal end, connected to the delivery unit 4, thus allowing a direct connection between the drive means 2 and the delivery unit 4.

In greater detail, the connection means 3 allow the direct transfer of the first fluid PF from the drive means 2 to the delivery unit 4.

The transfer of the first fluid PF takes place thanks to the rotation operation of the knob 7 described earlier.

Such connection means 3 can be in the form of a tube. For example, such a tube can consist of inelastic plastic material, like for example polyamide, which allows an unaltered transfer of forces from the drive means 2 to the delivery unit 4.

According to a version of the present invention, the tube of the connection means 3 can be constrained, at the first distal end thereof, to the nozzle U of the drive means 2, and removably associated, at the second proximal end thereof, with the delivery unit 4.

The tube can be constrained to the nozzle U, for example, through welding, gluing or analogous ways suitable for the purpose.

The tube can be associated with the delivery unit 4 through a bayonet type of connection or similar.

According to a further version of the present invention, the connection means 3 can be removably connected to the drive means 2 and to the delivery unit 4, at the first distal end and at the second proximal end, respectively.

Moreover, the tube can have a small diameter, for example equal to 0.3-1 mm, so as to be flexible and to contain a minimum dead volume of first fluid PF. The tube therefore houses little first fluid PF.

The hydraulic extrusion system 1 further comprises a delivery unit 4.

The delivery unit 4 acts as a container and dispenser of the bone cement CO or of the medical or chemical substance contained in it.

Moreover, the delivery unit 4 is made of a light material, i.e. such as not to be weighty when the delivery unit 4 is positioned, for example, close to the patient.

The delivery unit 4 comprises a cartridge. Such a cartridge is preferably substantially cylindrical. Such a cartridge is a small container or body or chamber capable of housing the bone cement CO or another medical or chemical substance.

The cartridge can receive an amount of bone cement CO or other medical or chemical substance of the order of 10 ml.

Such a cartridge is compact and small in size but, in a version of the invention, it has a circular cross section of large diameter, with respect to its longitudinal dimension.

The cartridge has, indeed, a short development in height, in order to reduce the vertical or longitudinal bulk thereof. For example, a minimum development in height reduces the risk of bone damage or of contact with the diagnostic means positioned close to the patient.

The cartridge is capable of withstanding great pressures, even over 100 bar. In addition, the material from which the cartridge is made is capable of containing most medical and chemical fluids on the market.

The cartridge can, in a version of the invention, be made of transparent plastic material, so as to monitor the insertion and the subsequent delivery of the bone cement CO or of the other medical or chemical substance.

In addition, the cartridge is capable of withstanding most medical and chemical fluids present on the market.

The cartridge consists of and comprises a bottom 11, adapted for being connected to the connection means 3 and one or more side walls 13.

In particular, when such a cartridge has a cylindrical configuration, it comprises a sole and unique side wall 13.

Such a delivery unit 4 or such a cartridge comprises a connection zone 14, at the bottom 11, a first chamber 15, a second piston 16, a delivery chamber 17 and an output channel 18.

The cartridge of the delivery unit is made in a single body, consisting at least of the bottom 11 and the one or more side walls 13 and the aforementioned chambers or zones can be defined inside the single body itself.

The cartridge of the delivery unit is made in a single body also with the connection zone 14.

The connection zone 14, indeed, is a zone defined in the bottom 11 of the cartridge and not a separate element with respect to the cartridge itself.

Such a delivery unit 4 or such a cartridge can also comprise a Luer connection 19 and a lid 20.

According to a version of the present invention, the lid 20 can be removably connected to the cartridge.

For example, the lid 20 can be screwed onto the cartridge.

According to a further version of the present invention, the lid 20 can be constrained to the cartridge.

The bottom 11 contains an opening that defines the connection zone 14.

The connection zone 14 allows the connection between the connection means 3 and the cartridge and thus allows the passage of the first fluid PF from the connection means (thus from the syringe 5 of the drive means 2) to the delivery unit 4.

The first chamber 15 is an area that is located at and is connected with the connection zone 14.

Such a first chamber 15 is confined at the bottom by the bottom 11, at the top by the second piston 16 and laterally by the one or more side walls 13.

The first chamber 15 constitutes the distal portion (with respect to the delivery opening of the bone cement CO or of the other medical or chemical substance) of the cartridge or of the delivery unit 4.

The fluid PF, once it has passed through the connection zone 14, goes to fill up the first chamber 15.

The first chamber 15 thus houses the first fluid PF pushed by the drive means 2 through the connection means 3.

The one or more side walls 13 laterally confine the first chamber 15, the second piston 16 and the delivery chamber 17.

Such side walls 13 are of a sufficient thickness to ensure good resistance to the high pressures acting in the hydraulic extrusion system 1.

In greater detail, the one or more side walls 13 are connected and joined to the bottom 11, and, in a version of the invention, have at least one upper or proximal free edge (with respect to the delivery opening of the bone cement CO or of the other medical or chemical substance), i.e. in an opposite position with respect to the bottom 11.

Figure 3:
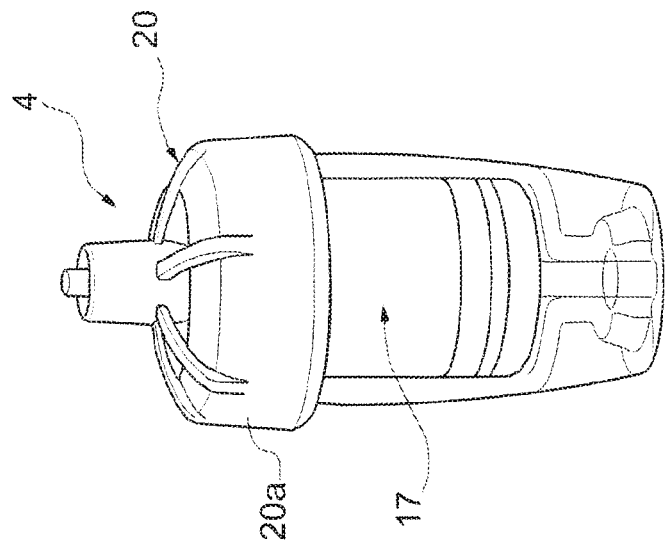
FIG. 3 is an exploded perspective view of a component or delivery unit of the hydraulic extrusion system according to the present invention.
Figure 4:
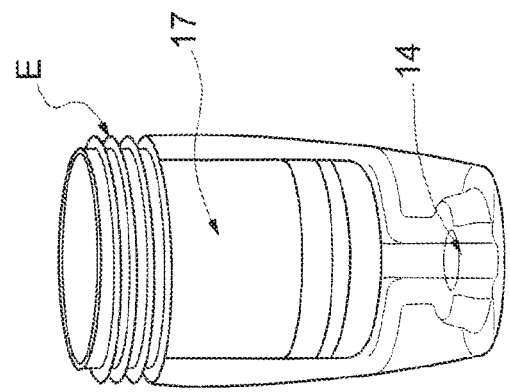
FIG. 4 is an assembled perspective view of the component of FIG. 3.

At such at least one free edge E, as shown in FIG. 3, there can be a threading arranged externally with respect to the at least one side wall 13 of the cartridge.

Figure 8:
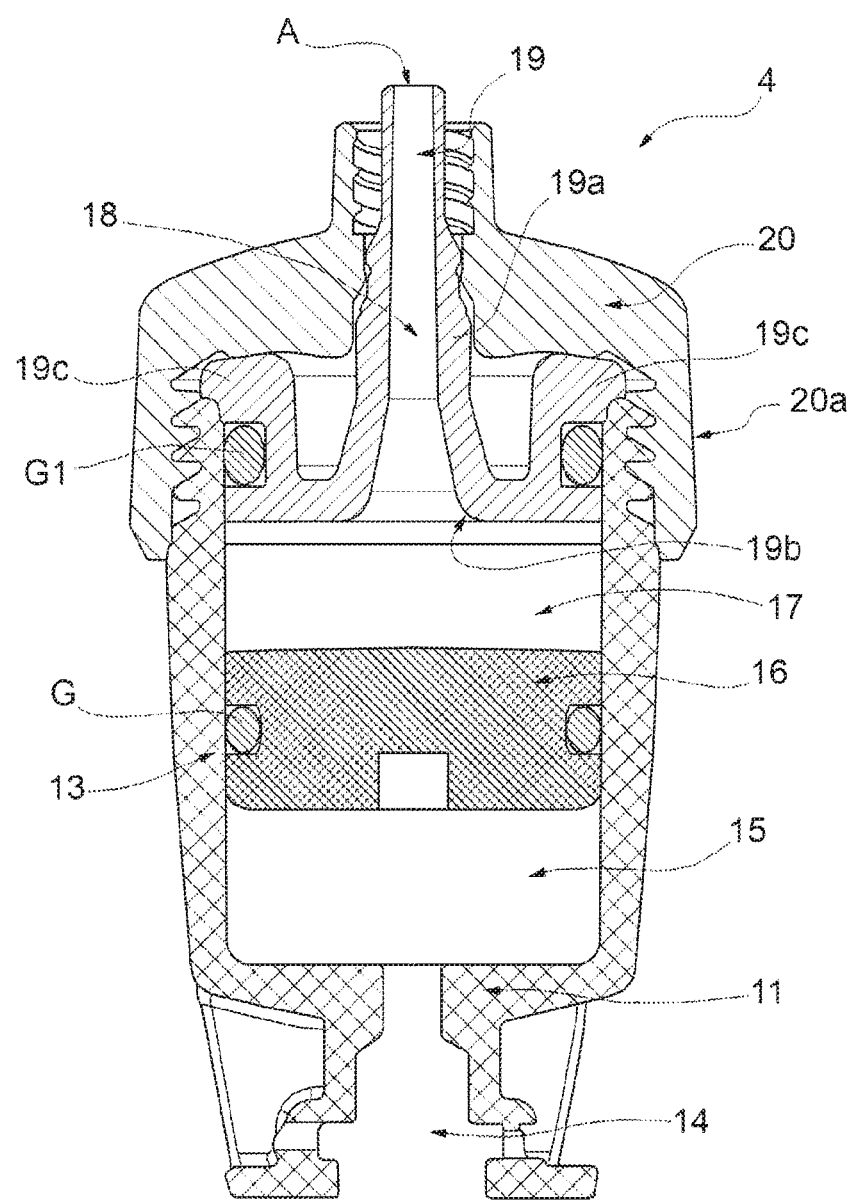
FIG. 8 is a section view of the delivery component or unit according to FIGS. 3 and 4.
Figure 9:
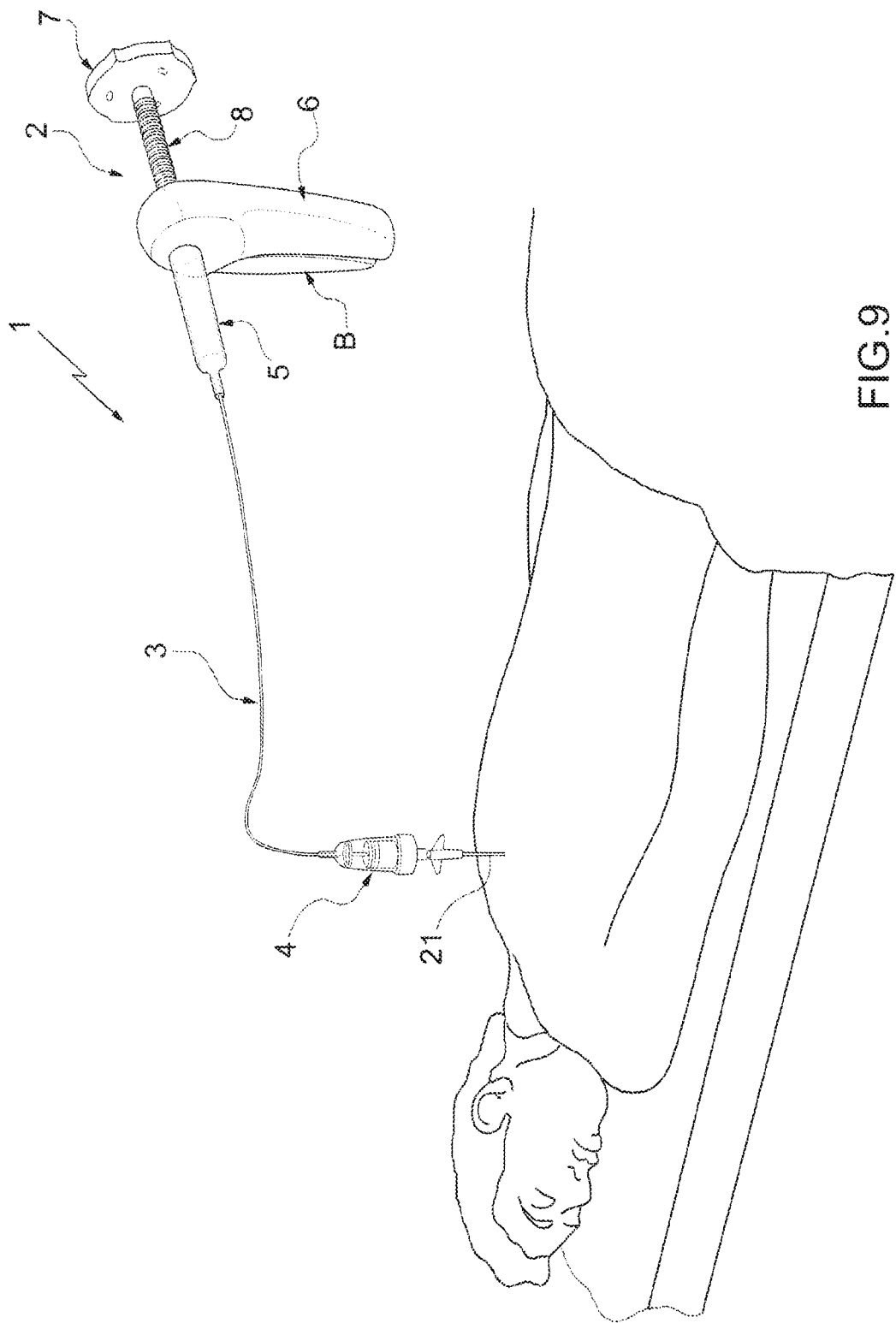
FIG. 9 shows a possible use of the hydraulic extrusion system.
Figure 10:
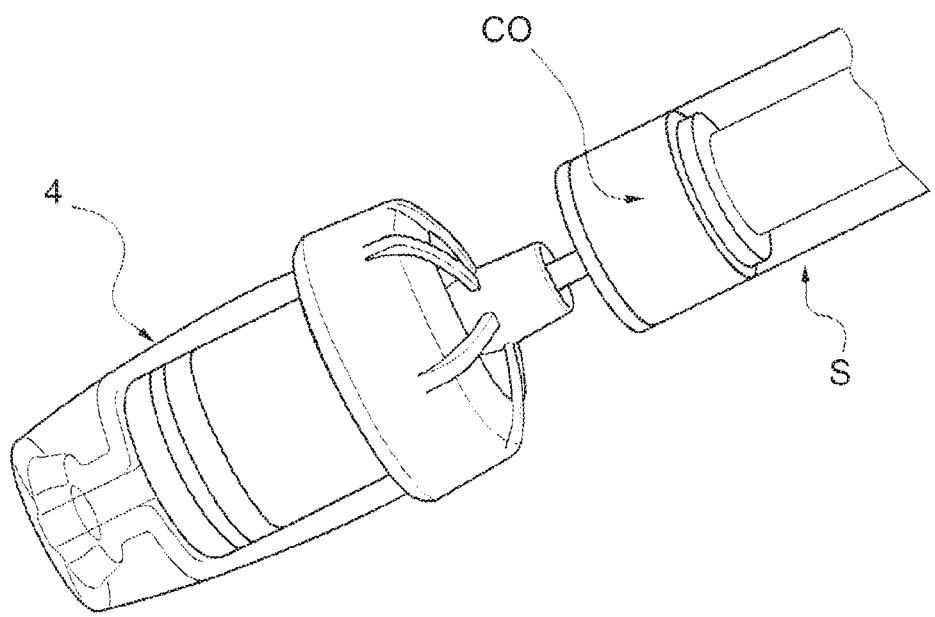
FIG. 10 shows a way of loading the delivery component or unit of FIG. 8.

The delivery unit 4 or the cartridge comprises a second piston 16, as stated and as it is shown in FIG. 8. Such a second piston 16 is housed inside the cartridge and is adapted, in use, for sliding inside it.

The second piston 16 transversally separates the first chamber 15 and the delivery chamber 17; in particular, the second piston 16 upperly or proximally confines the first chamber 15.

As well as spatially separating the first chamber 15 and the delivery chamber 17, the second piston 16 separates the first fluid PF and the bone cement CO or the other substance present in the delivery chamber 17 in a fluid-tight manner Such a second piston 16 can be in the form of a mobile rigid disc.

The delivery chamber 17 is lowerly or distally confined by the second piston 16.

The second piston 16 is therefore a means for the physical and hydraulic separation between the first chamber 15 and the delivery chamber 17.

Moreover, the second piston 16 comprises a peripheral gasket G that allows such a physical and hydraulic separation between the first chamber 15 and the delivery chamber 17.

The delivery chamber 17 is an area adapted for containing the bone cement CO or other viscous fluids to be delivered, according to the field of use of the hydraulic extrusion system 1.

The delivery chamber 17 constitutes the proximal portion of the cartridge, at the zone that in use will be closer to the patient. The lid 20 is a closure element for the delivery chamber 17.

In particular, the lid 20 can be a component that is independent from the cartridge, and is adapted for removably associating with the at least one side wall 13.

The lid 20 has a cap component and comprises, in a substantially apex position thereof, an opening A or output channel 18.

The opening A or output channel 18 is arranged in proximal position with respect to the cartridge and is adapted to make the bone cement CO or the pharmaceutical or chemical substance comes out from the delivery chamber 17 or from the delivery unit 4.

The lid 20 has, at the peripheral edge thereof, a side wall 20a that extends distally from the cap component.

Such a side wall 20a of the lid 20 comprises an internal threading, adapted for screwing/unscrewing in use into/from the threading present at the free edge E of the cartridge.

The lid 20 can house a Luer connection 19, possibly of the standard type.

The Luer connection 19 has a wall 19a shaped substantially like a cone or frustum of cone that extends substantially from the opening A or output channel 18 up to the inner surface of the side wall 13 of the cartridge.

From the distal edge 19b of the wall 19a a counter-wall 19c extends with a substantially vertically elongation adjacent to the inner wall of the side wall 13. The counter-wall 19c has a free peripheral end at the free edge E of the cartridge of the delivery unit 4.

Perimetrically to the counter-wall 19c there is a fluid-tight annular gasket G1, arranged between the counter-wall 19c and the inner wall of the side wall 13 of the cartridge.

In this way, the lid 20 keeps fluid tight the zone between cartridge and lid 20 itself and allows, thanks to the opening A or output channel 18, the rigid and stable connection with a delivery needle 21.

The opening A or the output channel 18 allows the bone cement CO or the other medical or chemical substance to enter/exit the delivery chamber 17 and, in use, the needle 21.

The cartridge can be filled with bone cement CO or with another pharmaceutical or chemical substance by gravity filling or by injection.

In the first case, the lid is removed or unscrewed from the cartridge and the substance to be inserted is poured by gravity inside the cartridge, or rather into the delivery chamber 17.

According to the other way, the lid 20 is fixed or installed on the cartridge and, at the opening A or at the output channel 18, a tank or an external syringe S containing said substance is positioned. The latter is then injected inside the delivery chamber 17 of the cartridge of the delivery unit 4.

Such an external syringe S can be connected or constrained to the Luer connection 19.

This operation is carried out quickly and simply, thanks to the large diameter of the second piston 16 with respect to the diameter of the piston contained in the external syringe S.

Therefore, the bone cement CO or the other pharmaceutical or chemical substance can enter into the delivery chamber 17, during a loading operation of the cartridge, or can come out from the delivery chamber 17, during a delivery operation.

A delivery needle 21, as shown in FIG. 1, is rigidly connected to the cartridge through the Luer connection 19.

The delivery needle 21 can be fixed in the vertebral bone and allows, for example, the delivery of bone cement CO inside such a site.

The lid 20, possibly equipped with the Luer connection 19, in a version of the invention can be a single body with the cartridge of the delivery unit.

The Luer connection 19, according to a version of the invention, can be comprised and/or fixedly connected inside the lid 20. In this way, when the lid 20 is extracted or removed from the cartridge, the Luer connection 19 is also extracted together with the lid 20 itself.

Figure 6:
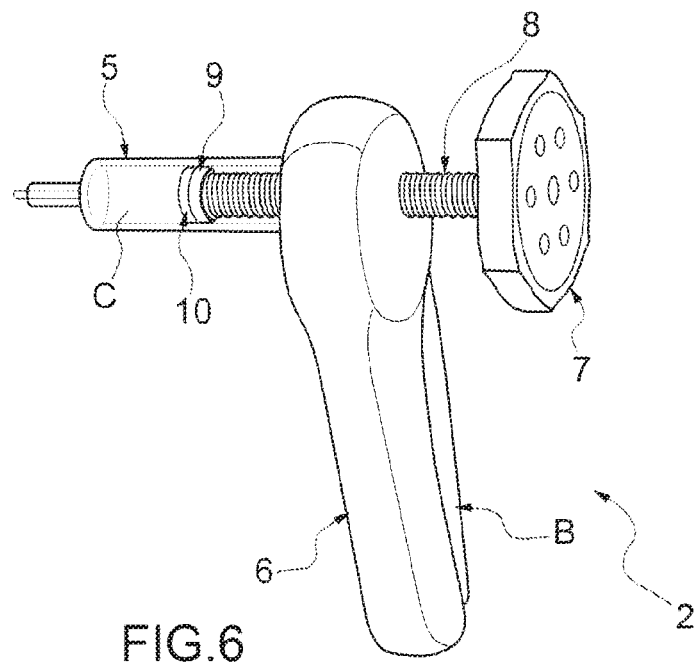
FIG. 6 is a perspective view of the drive means of FIGS. 5a and 5b.

The hydraulic extrusion system 1 during use in the medical field, as shown in FIG. 6, foresees an initial preparation step of the system 1 and a secondary delivery step of the bone cement.

During the preparation step of the system 1, the following are carried out: filling of the syringe 5 with the first fluid PF, loading of the cartridge through bone cement CO or other pharmaceutical or chemical substance, connection of one end of the connection means 3 to the nozzle U of the syringe 5, connection of the free end of the connection means 3 to the connection zone 14 of the cartridge of the delivery unit 4, connection of a delivery needle to the Luer connection 19 of the cartridge or of the lid 20.

The needle 21 is then, in use, inserted in the site to be treated and that must have the substance in question delivered to it.

In the delivery step of the bone cement CO or of the pharmaceutical or chemical substance, the rotation of the knob 7 is carried out, which allows the movement of the first piston 10 and the thrusting, by the latter, of the first fluid PF contained in the syringe 5.

The first fluid PF comes out through the nozzle U of the syringe 5, entering into the connection means 3.

The first fluid PF passes through the connection means 3 and reaches the connection zone 14 of the cartridge; then it enters the first chamber 15 of the cartridge and presses against the second piston 16.

The second piston 16 translates and pushes the bone cement CO or the other pharmaceutical or chemical substance contained in the delivery chamber 17; such substances then come out through the output channel 18 and the opening A, to reach the delivery needle 21.

The bone cement CO or the other pharmaceutical or chemical substance is delivered by the needle and reaches the bone area to be treated.

The invention thus conceived can undergo numerous modifications and variants, all of which are covered by the scope of the inventive concept.

Moreover, all of the details can be replaced by other technically equivalent elements. In practice, the materials used, as well as the contingent shapes and sizes, can be whatever according to the requirements, without for this reason departing from the scope of protection of the following claims.

The invention, thus conceived, allows technical advantages to be obtained.

An important technical advantage consists of the fact that the hydraulic extrusion system 1 allows a direct connection of the drive means 2 to the delivery unit 4, without the need to have elements arranged between them to carry out the correct operation of the system.

In a version of the invention, the hydraulic extrusion system 1 according to the present invention comprises only the drive means 2 (including the described hydraulic pump), the connection means 3 and the delivery unit 4 (including the cartridge, the lid 20 and the Luer connection 19), possibly equipped with the delivery needle 21.

In particular, the cartridge is connected directly to the connection means 3 and therefore to the drive means 2, without intermediate devices.

In this way, a hydraulic extrusion system 1 is obtained that is simpler to assemble, to use and to maintain.

Another advantage is linked to the configuration of the delivery unit 4, which is in the form of small, light and compact means. Such characteristics allow better handling of the system and the possibility of having a lighter tool to be positioned in the vicinity of the patient, in the case in which such a system 1 is used in the medical field.

A possible yet other advantage is linked to the fact that the hydraulic extrusion system 1, according to the present invention, makes it possible to receive a very large amount of bone cement CO with respect to conventional devices, i.e. of the order of 10 ml and this is thanks to the squat shape of the cartridge used.

In this way, it is possible to deliver a very large amount of bone cement, ensuring a prolonged use of the system 1, without the need to carry out frequent reloads of the cartridge.

Moreover, an important technical advantage consists of the fact that the cartridge or rather the second piston 16 has a very large section (with respect to the diameter of the connection means 3 and possibly of the syringe 5 and/or, particularly, of the first piston 10 thereof) that allows the hydraulic extrusion system 1 to act as force multiplier.

In greater detail, as shown in FIG. 11, by the principle of communicating vessels the pressure acting inside the drive means 2, the connection means 3 and the delivery unit 4 is the same. It is thus possible to calculate the force acting at the syringe 5 and that acting at the cartridge, remembering that the force is given by the product of the pressure by the area on which such a force acts.

For example, setting a diameter equal to 14.2 mm for the syringe 5 and, in the case of a cartridge having a circular section, a diameter equal to 25.75 mm for the cartridge itself, where the pressure P acting on the sections of syringe 5 and of cartridge is identical, a ratio is obtained equal to 3.3 between the force acting at the cartridge and that acting at the syringe 5. Such a ratio value demonstrates that there is a multiplication of the force, for example of about 3 times or more, and consequently the force exerted by the user to move the knob 7 and actuate the delivery is much less than that which would have been needed by acting directly on the cartridge.

In particular, the second piston 16 has a section or transversal area (with respect to the projection of the cartridge) that is larger than the section or area of the first piston 10 of the syringe 5, for example equal to at least double the section or area of the first piston 10 of the syringe 5 or, for example even more preferably, equal to at least three times the section or area of the first piston 10. In this way, the device according to the present invention is a force multiplier of at least double, or more preferably triple the pressure exerted by the drive means 2.

It has thus been seen how the invention achieves the proposed purposes.

The present invention has been described according to preferred embodiments, but equivalent variants can be devised without departing from the scope of protection offered by the following claims.

The invention claimed is:

1. A hydraulic extrusion system for delivering a fluid to be delivered, such as for example a viscous fluid or bone cement (CO) or a pharmaceutical or medical substance or a chemical substance, wherein said hydraulic extrusion system comprises drive means comprising a syringe and a plunger, wherein said syringe comprises a cavity (C) adapted to contain a first fluid (PF), wherein said syringe has a delivery nozzle (U) at a first end, connection means and a delivery unit, wherein said delivery unit comprises a cartridge, adapted to contain said fluid to be delivered, wherein said delivery unit or said cartridge comprises a bottom provided with a connection zone, placed at said connection means, at least one side wall, a first chamber, inside said cartridge and at said bottom, a delivery unit piston, a delivery chamber, inside said cartridge and placed in opposite position with respect to said bottom and adapted to contain said fluid to be delivered, and an opening (A) or an output channel, adapted to allow the delivery of said fluid to be delivered and/or to be associated with a delivery needle, wherein said connection means has a first distal end connected to said nozzle (U) of said drive means and a second proximal end, opposite to said first distal end, connected to and/or inserted in said delivery unit, wherein said delivery unit or said cartridge comprises a lid connected to said delivery unit or to said cartridge in a removable way, wherein said lid comprises a cap component and, in a substantially apical position of the lid, said opening (A) and/or said output channel.

2. The hydraulic extrusion system according to claim 1, wherein said second proximal end of the connection means is directly connected to said delivery unit.

3. The hydraulic extrusion system according to claim 1, wherein said delivery unit or said cartridge comprises a Luer connection.

4. The hydraulic extrusion system according to claim 1, wherein said bottom or said connection zone comprises an opening adapted to allow a communication of fluid between said first chamber and said connection means and adapted to allow the passage of the first fluid (PF) directly from the connection means to said first chamber.

5. The hydraulic extrusion system according to claim 1, wherein said delivery unit piston is placed internally and transversely to said cartridge, and/or wherein said delivery unit piston is a means of physical and hydraulic separation between said first chamber and said delivery chamber.

6. The hydraulic extrusion system according to claim 1, wherein said delivery unit piston has a wide cross sectional area compared with the cross section of said connection means and said syringe and/or wherein said delivery unit piston has a wide cross sectional area compared with the cross section of a piston of said plunger of said syringe and/or wherein said delivery unit piston has a cross sectional area of wider surface of at least two or of at least three times compared with the cross section of said piston of said plunger of said syringe.

7. The hydraulic extrusion system according to claim 1, wherein said lid comprises an opening (A) and/or an output channel adapted to allow the output or input of said fluid to be delivered from or in said delivery chamber.

8. The hydraulic extrusion system according to claim 1, wherein said lid comprises, at one peripheral edge thereof, a side wall that extends distally from said cap component, wherein said side wall comprises an internal thread, adapted to be screwed/unscrewed in use to an external thread present at a free edge (E) of said cartridge.

9. The hydraulic extrusion system according to claim 3, wherein said Luer connection comprises a wall with a substantially cone or frustum of cone elongation which extends substantially from said opening (A) and/or from said output channel up to the inner surface of said at least one side wall of said cartridge.

10. The hydraulic extrusion system according to claim 9, wherein said wall comprises a distal edge and a counter-wall which extends from said distal edge with a substantially vertical extension adjacent to an inner wall of said at least one side wall.

11. The hydraulic extrusion system according to claim 10, wherein said delivery unit piston and/or said counter-wall comprise an annular fluid-tight gasket (G, G1).

12. The hydraulic extrusion system according to claim 1, wherein said drive means comprises a handle comprising a lever (B) adapted to be positioned in a locking or unlocking configuration for the sliding or the rotation of said plunger and wherein said plunger comprises a knob, wherein when said lever (B) is in the locking configuration said knob can be rotated to operate the delivery of said first fluid (PF) from the drive means to the connection means, or when said lever (B) is in the unlocking configuration, said knob can be translated longitudinally to allow the suction of said first fluid (PF) in said drive means.

13. The hydraulic extrusion system according to claim 12, wherein said knob comprises a mechanism that allows it to limit the pressure and speed with which said first fluid (PF) is delivered at a predetermined maximum value.

14. The hydraulic extrusion system according to claim 1, wherein said connection means comprises a tube of flexible and inelastic material.

15. The hydraulic extrusion system according to claim 1, wherein said connection means is constrained to said drive means, at said first end, and are configured connectable in a removable manner to said delivery unit, at said second end.

* * * * *